United States Patent [19]

Christman et al.

[11] 4,106,982

[45] Aug. 15, 1978

[54] PRODUCTION OF CARRIER-FREE H$^{11}$CN

[75] Inventors: David R. Christman, Setauket; Ronald D. Finn, Westhampton Beach; Alfred P. Wolf, Setauket, all of N.Y.

[73] Assignee: The United States of America as represented by the United States Department of Energy, Washington, D.C.

[21] Appl. No.: 456,996

[22] Filed: Apr. 1, 1974

[51] Int. Cl.$^2$ .............................................. G21G 1/10
[52] U.S. Cl. ........................................ 176/11; 176/14
[58] Field of Search .................. 176/10, 11, 14, 16–29

[56] References Cited

PUBLICATIONS

Radiochimica Acta, Band 6, Heft 1, pp. 32–39, Aug. 1966, Ache et al.
NSA vol. 29, No. 1, Jan. 1974, p. 22, No. 217.
NSA vol. 26, No. 5, 3/15/72, p. 842, No. 8989.
NSA vol. 21, No. 1, Jan. 1967, p. 15, No. 120.

Primary Examiner—Harvey E. Behrend
Attorney, Agent, or Firm—Dean E. Carlson; Leonard Belkin

[57] ABSTRACT

A method of synthesizing H$^{11}$CN involving the proton irradiation of N$_2$ + H$_2$ to produce a mixture of $^{11}$CH$_4$ and NH$_3$ followed by the reaction of $^{11}$CH$_4$ and NH$_3$ to produce H$^{11}$CN and the separation of carrier free H$^{11}$CN.

6 Claims, 1 Drawing Figure

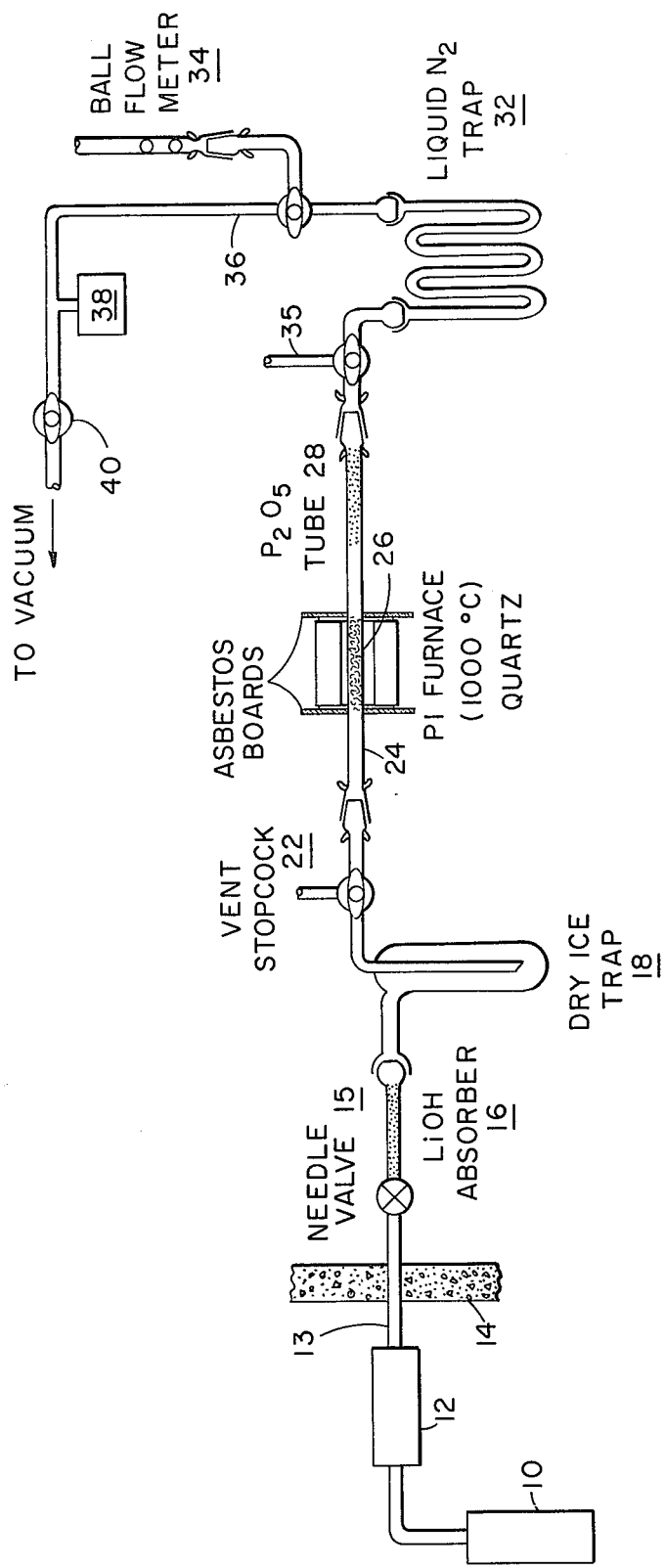

PRODUCTION OF CARRIER-FREE H¹¹CN

BACKGROUND OF THE INVENTION

The invention described herein was made in the course of, or under a contract with the U.S. Atomic Energy Commission.

Hydrogen cyanide labeled with carbon-11 has been demonstrated to have some direct medical use in such areas as blood volume measurements and in addition appears to have potential utility as great as carbon dioxide-$^{11}$C in the synthesis of radiopharmaceuticals. $^{14}$C-labelled pharmaceuticals have been used for pilot studies of organ distribution and compound metabolism. However, as $^{11}$C is a positron emitter and has a very short half life as compared to the beta emitting $^{14}$C, certain applications (e.g. organ scanning) are possible which cannot be done with $^{14}$C.

Several papers have appeared recently detailing some synthetic routes to H$^{11}$CN, as well as its direct production in a cyclotron target by recoil processes. However, all of the synthetic routes investigated heretofore are tedious and time consuming, and they all result in products containing various amounts of inactive carrier. In some of the applications, the H$^{11}$CN is useless unless it is essentially carrier free. The direct recoil process currently being used by some workers utilizes less than 50% of the C-11 produced, even under optimum conditions. It requires the heating of the target to about 250° C, and it gives rather erratic results. The process produces H$^{11}$CN directly by exposing N$_2$ and H$_2$ to proton irradiation at low dose levels, to avoid destruction of the cyanide. But yields are relatively low and the process is inefficient.

Another difficulty associated with some of the previous methods of producing this radioactive cyanide resides in the half life of 20.4 minutes for $^{11}$C. This relatively short half life makes a radiopharmaceutical labelled with this isotope useful for only about 3 hours in most applications. Therefore for cyanide to be useful in any synthesis process it must be capable of producing sufficient amounts of the organic end product within about one hour after cyclotron irradiation.

SUMMARY OF THE INVENTION

The present invention provides a rapid and reliable, online process for producing essentially carrier free H$^{11}$CN with uniformly excellent results and with much greater efficiency than has heretofore been possible.

It has been discovered that adequate yields with acceptable utilization of the radioactive cyanide can be obtained in accordance with the principles of this invention by subjecting a mixture of N$_2$ and H$_2$ to relatively high doses of proton irradiation to produce an intermediate of $^{11}$CH$_4$, followed by a reaction with NH$_3$ which is present as the result of the radiation in the target to produce ultimately the H$^{11}$CN within an acceptable time period so that it can be used as a tracer material or as a synthetic intermediate.

In accordance with a preferred embodiment of this invention, a gaseous mixture of nitrogen-14 and hydrogen is irradiated by a beam of protons having an energy in excess of 4 MeV and up to 28 MeV, producing an effluent containing NH$_3$, $^{11}$CH$_4$, and a trace of $^{11}$CO$_2$ and $^{11}$CO, removing the $^{11}$CO$_2$ from the effluent, and then reacting the $^{11}$CH$_4$ and the NH$_3$ in the effluent to form H$^{11}$CN and hydrogen. If desired, most of the excess NH$_3$ can be removed chemically after the last mentioned reaction, after which the remaining NH$_3$ and the target gases are removed by evacuation, leaving carrier free H$^{11}$CN as a salt.

It is thus a principal object of this invention to synthesize H$^{11}$CN with greater reliability and efficiency than heretofore has been possible.

Other objects and advantages of this invention will hereinafter become obvious from the following description of a preferred embodiment of this invention.

BRIEF DESCRIPTION OF THE DRAWING

The FIGURE illustrates schematically apparatus employed in an example of this invention.

DESCRIPTION OF THE PREFERRED EMBODIMENT

This invention provides a method for the preparation of essentially carrier free H$^{11}$CN, based on the production of $^{11}$CH$_4$ directly in a cyclotron target, which is then quantitatively converted to H$^{11}$CN in the presence of ammonia.

A target gas consisting of an oxygen free mixture of nitrogen-14 up to 97 vol % and the balance hydrogen is irradiated with protons having an energy in excess of 4 MeV, which is the threshold for the $^{14}$N(p,α)$^{11}$C reaction. By oxygen-free is meant that oxygen is present in amounts no greater than 2 ppm. Preferably, the target gas mixture is subjected to protons up to but not in excess of 18 MeV, and for maximum efficiency the protons are attenuated to 4 MeV. Above 18 MeV, undesirable nuclides such as $^7$Be begin to be produced. This range of proton energy covers the entire region of maximum cross section for this reaction as described in Phys. Rev. C 3; 2167-2171, 1971.

While the pressure of the target gas is not critical to the process, the most efficient operation is to have the pressure adjusted so that the proton energy is degraded to 4 MeV at the back of the target.

As a result of this irradiation, there is produced an effluent gas stream with the products in the gas mixture consisting largely of $^{11}$CH$_4$ and NH$_3$, the latter by radiolysis. The ammonia, which is present in an amount about 10$^6$ times that of the $^{11}$CH$_4$, is useful as further described in the conversion of the $^{11}$CH$_4$ to H$^{11}$CN.

The effluent is then treated for the removal of any $^{11}$CO$_2$ which may be present due to the presence of O$_2$ in the target gas, followed by cold trapping with dry-ice to remove any water present. Removal of $^{11}$CO$_2$ may be done with a LiOH absorber or other basic absorber.

The mixture of $^{11}$CH$_4$ and NH$_3$ is then heated in the presence of Pt metal to a temperature not in excess of 1100° C with a preferred range of 975 to 1100° C to permit the following reaction to occur:

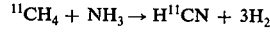

Most of the remaining NH$_3$ is removed by absorption(via P$_2$O$_5$) and a liquid N$_2$ trap may then be employed to trap the resultant carrier free H$^{11}$CN and remaining NH$_3$. This NH$_3$ may be separated from the H$^{11}$CN by any convenient or conventional method. If the H$^{11}$CN is absorbed in aqueous base, the NH$_3$ is removed by evacuation to dryness.

The target gas of nitrogen and hydrogen would as a practical matter employ normal or naturally occurring nitrogen and hydrogen. Nitrogen contains 0.37% of nitrogen-15 which upon irradiation is converted to $^{12}$C, the most abundant stable carbon isotope and its presence in such amount does not interfere with the process or in the use of the resultant product. Similarly, the deuterium and tritium isotopes of hydrogen present in the normal amounts do not interfere with the process or the use of the resultant product. A maximum volume % of nitrogen in the target gas is 97%, as above this level the production of methane drops sharply due to an insufficiency of hydrogen, and the process would lack usefulness. While the process will function with reduced amounts of nitrogen the process is wasteful if the amount employed drops too low, so that a preferred range for the nitrogen is 95–97 vol %. Yields drop linearly with reductions in the amount of nitrogen present, since the nitrogen is the direct source of the $^{11}$C in this process.

Oxygen present in the target gas in amounts above 2 ppm cuts yields sharply. The oxygen produces $^{11}CO_2$ and water during the irradiation. A grade of gas containing the miminum possible amount of hydrocarbon impurity, not to exceed 1 ppm, should be used in preparing the target gas mixture.

EXAMPLE

Referring to the drawing, the target gas consisting of an oxygen free (i.e. less than 2 ppm $O_2$) mixture of 95% $N_2$ and 5% $H_2$ was furnished pre-mixed from a tank 10 and fed into the Brookhaven National Laboratory 60 inch cyclotron target 12 at a pressure of 150 psi (total pressure 11 atm). There it was irradiated with 25 MeV protons in a 28 cm. long water cooled aluminum target. The incident protons were degraded to 18 MeV by a 60 mil spherical, aluminum front window and attenuated in the target gas to 4 MeV. The effluent gas from the target was brought into a laboratory adjacent to the cyclotron vault by means of 1/8 inch tubing 13 passing through concrete shielding wall 14. The flow rate was 250 cc/min as controlled by the needle valve 15 which also limited the pressure to 1 atm. in the remainder of the system. The gas passed over a lithium hydroxide absorber 16, to remove any $^{11}CO_2$ which was present (this was less than 2% of the total $^{11}$C activity in all cases), through a dry ice trap 18 to remove any moisture present, then through a vent stopcock 22 into a tube 24 containing 15 g. of $\leq 8$ mil platinum wire wound to fill an 8 cm path in a 1 cm OD quartz tube 26. This was held at 1000° C during production. The gas then passed through an 8 cm tube 28 of granular acidic absorbing material $P_2O_5$, to remove some of the excess ammonia present which came from radiolysis in the target. The $H^{11}CN$ and remaining $NH_3$ in the target gas was then trapped in a glass radiator trap 32 held at liquid nitrogen temperature. The remaining target gas was passed through a ball type flow meter 34 before escaping.

At the end of an irradiation, the gas was allowed to flow for 6 minutes, to flush most of the active products out of the target itself. It was then allowed to vent before the Pt furnace, and trap 32 was evacuated after closing stopcock 35, via a small vacuum line 36 which follows trap 32. After two minutes of pumping, stopcock 40 was closed and the active gas was distilled through vacuum line 36 into a synthesis vessel 38, by warming trap 32 electrically or with hot water and cooling vessel 38 with liquid nitrogen. The essentially carrier-free material was then absorbed in vessel 38 by a small amount of NaOH base (at least 0.05 N). If carrier is to be used, a solution of NaCN without added base can also be used for the absorpion of the material. In either case, some $NH_3$ is still present in he material, and it can be removed efficiently, if necessary, by pumping the solution to dryness after the $H^{11}CN$ has been absorbed in the base or carrier. Little activity is lost in this way, and if the absorbing solution has a volume of 100 $\lambda$, the process takes roughly two minutes. Therefore, the material can be present in synthesis vessel 38 ready for use within 12 minutes after the end of bombardment. Alternatively, the $H^{11}CN$ can be trapped directly in either basic or cyanide carrier solution by bubbling the gas through the solution during the run. Because of the high flow rate, however, a minimum of about 5 ml of solution is required in this case, and appreciable ammonia is then present in the final solution.

In the example just described, the $H^{11}CN$ was available in the gas phase or in basic solution, within 10–12 minutes after the end of the irradiation. With a current of 30 $\mu$A of focused 25 MeV protons impinging on the target, 2 curies of carrier-free $H^{11}CN$ were produced with a 45-min. irradiation. The material was then used in the preparation of carrier-free dopamine-$^{11}$C and norepinephrine-$^{11}$C for animal studies. Further information on the use of the resultant product is described in BNL 18073.

It is thus seen that there has been provided a method for the routine production of useful amounts of carrier-free, high activity $H^{11}CN$ and that the product is made available within 15 minutes after irradiation and within one hour after the beginning of irradiation.

What is claimed is:

1. The method of synthesizing $H^{11}CN$ comprising the steps of:
   a. subjecting a gaseous mixture of nitrogen and hydrogen to irradiation by a beam of protons having an energy in the range of about 4 to 18 MeV to induce the $^{14}N(p,\alpha)^{11}C$ reaction and produce an effluent containing $NH_3$ and $^{11}CH_4$;
   b. reacting the $^{11}CH_4$ and $NH_3$ in said effluent to form $H^{11}CN + H_2$; and
   c. removing the $H_2$, $N_2$ and remaining $NH_3$ to obtain $H^{11}CN$.

2. The method of claim 1 in which the gaseous mixture contains oxygen not in excess of 2 ppm and after irradiation any resultant $^{11}CO_2$ is removed prior to reaction of the $^{11}CH_4$ and $NH_3$ in the effluent.

3. The method of claim 2 in which the effluent contains excess amount of $NH_3$ required for the subsequent reaction of the latter with $^{11}CH_4$, and most of said excess is removed after the aforesaid reaction.

4. The method of claim 3 in which said gaseous mixture is under a pressure sufficient to maintain the energy of said protons in the range of 4 to 18 MeV.

5. The method of claim 3 in which the nitrogen in the target gas mixture is not in excess of 97 vol %.

6. The method of claim 3 in which the nitrogen in the target gas mixture is present in the range of 95 – 97 vol %, the balance being hydrogen.

* * * * *